US009055929B2

(12) United States Patent
Cuny

(10) Patent No.: US 9,055,929 B2
(45) Date of Patent: *Jun. 16, 2015

(54) LONG ULTRASONIC CUTTING BLADE FORMED OF LAMINATED SMALLER BLADES

(71) Applicant: Covidien LP, Mansfield, MA (US)

(72) Inventor: Douglas J. Cuny, Bethel, CT (US)

(73) Assignee: Covidien LP, Mansfield, MA (US)

( * ) Notice: Subject to any disclaimer, the term of this patent is extended or adjusted under 35 U.S.C. 154(b) by 407 days.

This patent is subject to a terminal disclaimer.

(21) Appl. No.: 13/681,799

(22) Filed: Nov. 20, 2012

(65) Prior Publication Data

US 2013/0079771 A1     Mar. 28, 2013

Related U.S. Application Data

(63) Continuation of application No. 10/491,023, filed as application No. PCT/US02/32685 on Oct. 11, 2002, now Pat. No. 8,328,833.

(60) Provisional application No. 60/328,597, filed on Oct. 11, 2001.

(51) Int. Cl.
    *A61B 17/32*   (2006.01)
    *A61B 18/00*   (2006.01)
    *A61B 17/22*   (2006.01)

(52) U.S. Cl.
    CPC ......... *A61B 18/00* (2013.01); *A61B 17/320068* (2013.01); *A61B 17/320092* (2013.01); *A61B 2017/22015* (2013.01);

(Continued)

(58) Field of Classification Search
    CPC ............... A61B 17/320068; A61B 17/320092; A61B 18/00; A61B 2017/22015; A61B 2017/22018; A61B 2017/320072; A61B 2017/320076
    USPC ............... 606/32–52, 169; 601/2, 3; 600/471; 604/22
    See application file for complete search history.

(56) References Cited

U.S. PATENT DOCUMENTS

| 5,474,530 A | 12/1995 | Passafaro et al. |
| 5,630,420 A | 5/1997 | Vaitekunas |
| 6,228,046 B1 | 5/2001 | Brisken |

(Continued)

OTHER PUBLICATIONS

International Search Report for PCT/US02/32685 date of completion Jan. 10, 2003 (3 pages).

(Continued)

*Primary Examiner* — David Eastwood

(57) ABSTRACT

An end effector of an ultrasonic surgical instrument is provided, the ultrasonic surgical instrument having a manipulatable structure, a body portion operatively connected to the manipulatable structure and having a distal end, a transducer, and the end effector being supported on the distal end of the body portion, the end effector including a plurality of resonant member elements, each resonant member operatively connected to a transducer of the plurality of transducers for effecting vibrations along the length of the resonant member, and including an operating surface configured to effect tissue dissection, cutting, coagulation, ligation and/or hemostasis, wherein a displacement curve associated with the vibrations of a first one of the plurality of resonant members is offset relative to the displacement curve associated with the vibrations of a second one of the plurality of resonant members.

9 Claims, 6 Drawing Sheets

(52) U.S. Cl.
CPC .......... *A61B 2017/22018* (2013.01); *A61B 2017/320072* (2013.01); *A61B 2017/320076* (2013.01)

(56) References Cited

U.S. PATENT DOCUMENTS

| | | |
|---|---|---|
| 6,292,702 B1 | 9/2001 | King et al. |
| 6,337,998 B1 | 1/2002 | Behl et al. |
| 6,387,109 B1 | 5/2002 | Davison et al. |
| 6,461,350 B1 | 10/2002 | Underwood et al. |
| 6,522,932 B1 | 2/2003 | Kuzma et al. |
| 6,926,712 B2 | 8/2005 | Phan |
| 6,984,220 B2 | 1/2006 | Wuchinich |
| 8,137,371 B2 | 3/2012 | Cuny |
| 8,241,312 B2 | 8/2012 | Messerly |
| 8,292,888 B2 | 10/2012 | Whitman |
| 8,328,833 B2 * | 12/2012 | Cuny .................. 606/169 |
| 2004/0162551 A1 | 8/2004 | Brown et al. |
| 2008/0009927 A1 | 1/2008 | Vilims |
| 2009/0012513 A1 | 1/2009 | Utley et al. |

OTHER PUBLICATIONS

Patent Abstracts of Japan vol. 007, No. 154 (E-185), Jul. 6, 1983 & JP 58 063300 A, (Keisuke Honda), Apr. 15, 1983.
Lal A. et al.: "Micromachined Silicon Needle for Ultrasonic Surgery", Ultrasonics Symposium, 1995. Proceedings, 1995 IEEE Seattle, WA, USA Nov. 7-10, 1995, New York, NY USA IEEE, US, pp. 1593-1596 XP010157413 ISBN: 0-7803-2940-6.
The Random House College Dictionary (1980) New York, p. 752.
European Search Report dated Sep. 17, 2014 issued in EP Application No. 12 82 6377.

* cited by examiner

LONG ULTRASONIC CUTTING BLADE FORMED OF LAMINATED SMALLER BLADES

CROSS-REFERENCE TO RELATED APPLICATIONS

This application is a continuation of U.S. application Ser. No. 10/491,023, filed on Mar. 25, 2004, which is a 371 of application No. PCT/US02/32685 filed Oct. 11, 2002, which claims benefit of application No. 60/328,597 filed Oct. 11, 2001, and the disclosures of each of the above-identified applications are hereby incorporated by reference in their entirety.

BACKGROUND

1. Technical Field

The present disclosure relates generally to ultrasonic surgical instruments. More specifically, the present disclosure relates to ultrasonic surgical instruments having an end effector configured to effect tissue dissection, cutting, coagulation, ligation and/or hemostasis, which instrument can be used in open as well as laparoscopic or endoscopic surgical procedures.

2. Background of Related Art

The use of ultrasonic instruments for surgical procedures including dissecting, cutting, ligating, effecting coagulation in, and/or effecting hemostasis in tissue and the benefits associated therewith are well known. For example, the use of an ultrasonic generator in conjunction with a surgical scalpel facilitates faster and easier cutting of organic tissue. Furthermore, heat generated by frictional contact between the scalpel blade and the body tissue, as the scalpel blade is vibrated at a high frequency, accelerates blood vessel clotting in the area of the cut, i.e., accelerates coagulation. The speed of heat generation is controlled by two factors, namely the frequency of the oscillations generated by the system, (determined by the manufacturer), and the amplitude or distance of movement of the oscillations as the blade is moved (determined by the user).

Advantages associated with ultrasonic surgical instruments include minimal lateral thermal damage, speed, absence of creation of an electrical circuit through the patient, and absence of unwanted byproducts such as smoke. Ultrasonic surgical instruments are suitable for traditional open surgical procedures and are particularly suitable for minimally invasive surgery such as laproscopic and endoscopic surgery.

An ultrasonic surgical instrument typically includes a manipulatable structure, such as a hand piece, having an ultrasonic transducer connected to an end-effector, such as a cutting/coagulating blade, via a vibration coupler that conducts ultrasonic frequency longitudinal vibrations from the ultrasonic transducer to the end-effector.

The ultrasonic displacements, i.e., amplitude of the vibrations transmitted from the transducer to the end-effector are sinusoidal by nature. The sinusoidal motion of the vibrations of the blade is a limiting factor that constrains the effective length of the blade. At the points along the sinusoidal curve where the amplitude is equal to zero, there is zero motion of the blade. To avoid areas of zero motion along the blade, a blade shorter than ½ wavelength of the oscillations is used. Currently the maximum blade length of a blade without zero motion areas is approximately 0.250".

Alternatively, a longer blade is used having areas of maximum motion, as well as areas of no motion along the length of the vibrating blade. The areas of no motion decrease the effective length of the blade, decreasing efficiency of the blade, and thus undesirably increasing the time needed to complete the surgical procedure.

Furthermore, there are large variations in amplitude along the length of the blade due to the sinusoidal nature of the oscillations, resulting in inconsistent behavior of the blade, and a lack of uniform operative results along the length of the blade. Uniformity is desirable for an even rate of cutting and coagulation, allowing the surgeon to proceed with the cutting procedure at an even rate and providing the surgeon with the ability to reliably predict results of operation of the surgical device.

Accordingly, the need exists for a decrease in operative time by increasing efficiency of the end-effector by increasing the effective length of the end-effector by reducing zero points along the sinusoidal amplitude curve. Furthermore, there is a need for increased consistency of behavior of the end-effector for obtaining uniform operative results along the length of the end-effector. Finally, the need exists for an ultrasonic surgical instrument configured using Micro Electrical Mechanical Systems (MEMS) technology in which the instrument is reduced in size and weight while increasing the effective length and behavior consistency of the end effector.

SUMMARY

An end effector of an ultrasonic surgical instrument is provided, the ultrasonic surgical instrument having a manipulatable structure, a body portion operatively connected to the manipulatable structure and having a distal end, a plurality of transducers, and the end effector being supported on the distal end of the body portion, the end effector including a plurality of resonant members, each resonant member operatively connected to a transducer of the plurality of transducers for effecting vibrations along the length of the resonant member, and including an operating surface configured to effect tissue dissection, cutting, coagulation, ligation and/or hemostasis, wherein a displacement curve associated with the vibrations of a first one of the plurality of resonant members is offset relative to the displacement curve associated with the vibrations of a second one of the plurality of resonant members.

In a preferred embodiment, the plurality of resonant members is a laminate, where the laminate preferably provides a flexible bond, with the first resonant member staggered longitudinally relative to the second resonant member. Preferably, the transducer includes first and second transducers operatively connected to the first and second resonant members, respectively.

In another preferred embodiment, each resonant member includes a frame and a resonant structure, wherein the transducer is operatively connected to the resonant structure, and the resonant structure includes the operating surface, wherein the proximal end of the resonant structure of the first resonant member is preferably staggered relative to the proximal end of the second resonant member. Preferably, the first resonant member further includes a transducer of the plurality of transducers, and the further included transducer is positioned in contact with the resonant structure of the first resonant member.

BRIEF DESCRIPTION OF THE DRAWINGS

The accompanying drawings, which are incorporated in and constitute a part of this specification, illustrate embodiments of the invention and, together with a general description of the invention given above, and the description of the embodiments given below, serve to explain the principles of the invention.

DETAILED DESCRIPTION

Figure 1A:
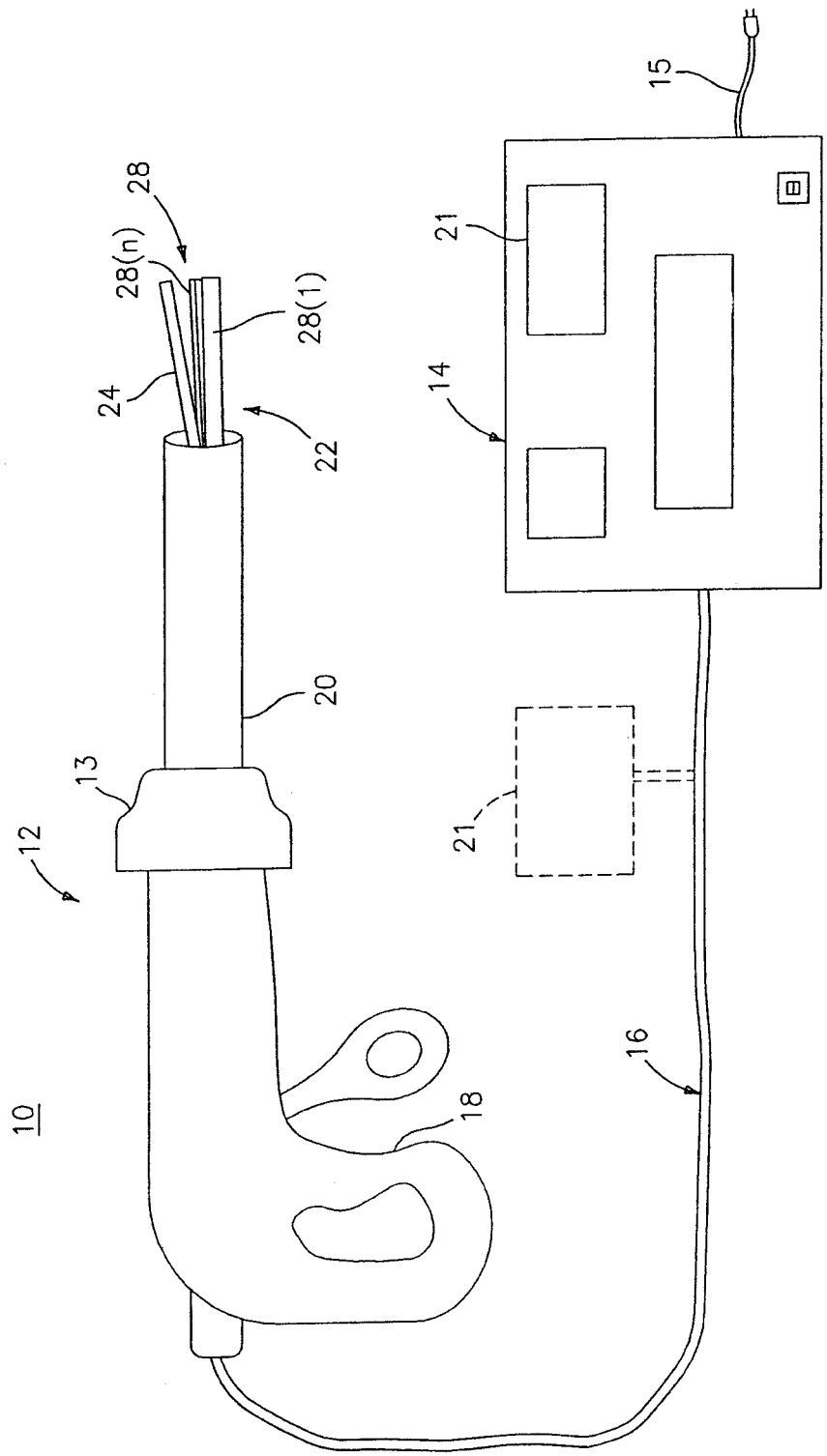
FIG. 1A is a schematic representation of one embodiment of the presently disclosed ultrasonic surgical system including a surgical instrument for cutting, dissecting, ligating, coagulating and/or effecting hemostasis in tissue.

An ultrasonic surgical instrument for effecting a surgical procedure at an end effector is provided, in which the end effector includes an array of staggered elements, where the staggering is configured so that displacement curves associated with displacement of each element are offset with respect to one another for collectively maximizing effective operation and consistency of operation of the array of elements.

Preferred embodiments of the presently disclosed ultrasonic surgical instrument will now be described in detail with reference to the drawings, in which like reference numerals designate identical or corresponding elements in each of the several views.

Figure 1B:
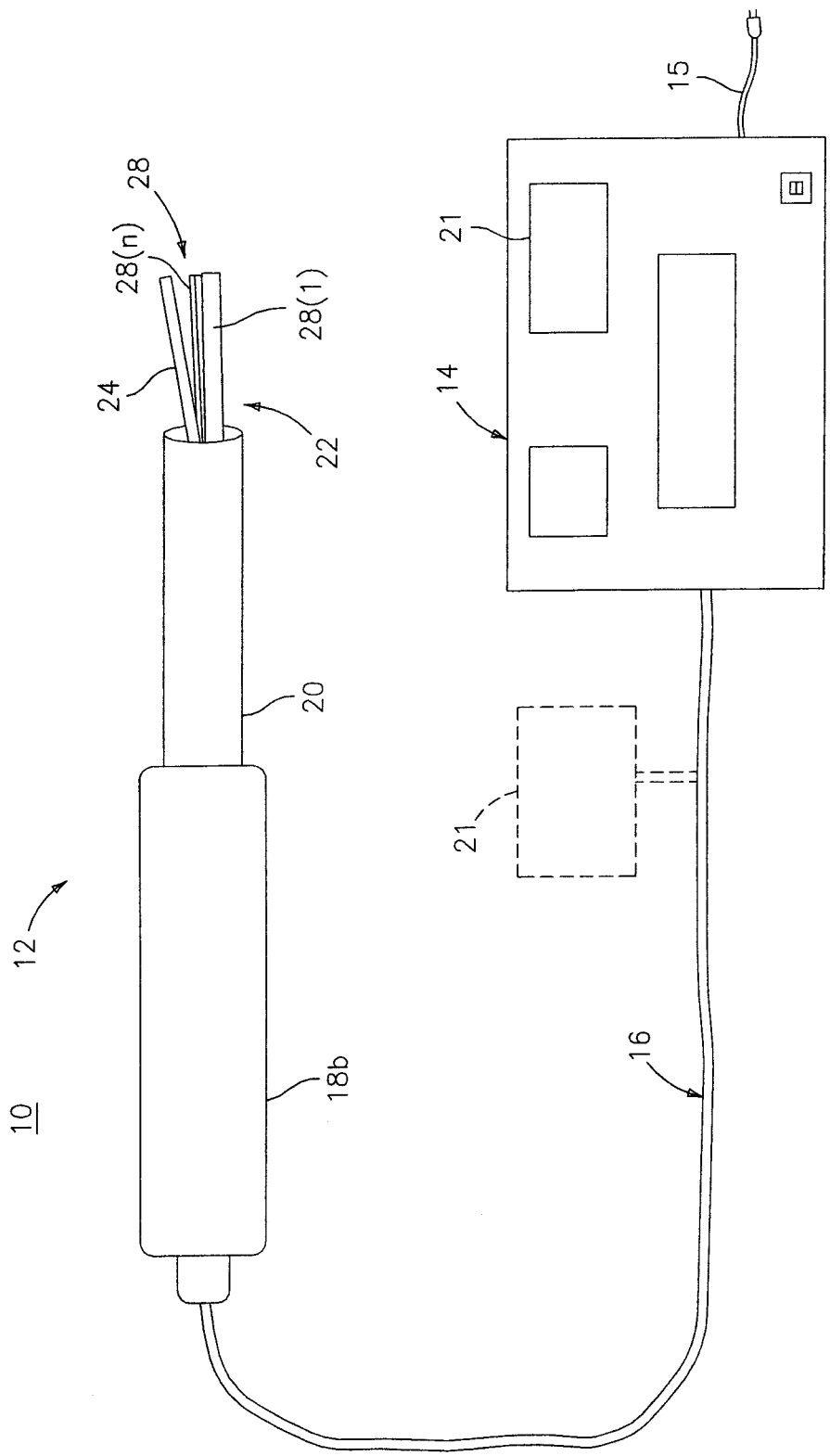
FIG. 1B is a schematic representation of another embodiment of the presently disclosed ultrasonic surgical system.

FIGS. 1A and 1B illustrate schematic views of first and second embodiments, respectively, of exemplary ultrasonic surgical system shown generally as 10. System 10 includes an ultrasonic instrument 12, a control module 14 and conductive cable 16 interconnecting ultrasonic instrument 12 to control module 14. Ultrasonic instrument 12 may be configured for open, endoscopic or laparoscopic surgical procedures and includes an elongated body 20, an end effector 22, and a manipulatable structure 18 operatively connected to the body 20 and/or the end effector 22 for manipulating the body and/or the end effector 22. The manipulatable structure 18 shown in FIG. 1A is a handle assembly 18a having a pistol grip configuration, although other handle configurations are envisioned, e.g., in-line handle, pencil grips, standard scissor grips, new ergonomically designed grips, etc. Rotation knob 13 may be provided to facilitate rotation of elongated body 20 in a known manner.

Manipulatable structure 18 shown in FIG. 1B is a robotic system 18b that manipulates the body and/or the end effector 22 in accordance with control signals received via cable 16. Preferably, the robotic system 18b includes a control module and a manipulation module (not shown), where the control module receives the control signals and controls the manipulation module to effect the desired manipulations in accordance with the control signals. At least one of the control module and the manipulation module may be located remotely from the rest of the ultrasonic instrument 12.

In another embodiment (not shown) the body 20 is omitted from the ultrasonic instrument 12 and from the manipulatable structure 18, and the end effector 22 is mounted to the manipulatable structure 18. In a different embodiment (not shown) the body 20 houses the manipulatable structure 18. In still another embodiment, at least a portion of the manipulatable structure is located in or on a module remotely located from the ultrasonic instrument 12. In yet a different embodiment (not shown) the body 20 includes an elongated flexible member extending distally from the remotely located module to the end effector 22.

End effector 22 includes a plurality of staggered resonant members $28(x)$, preferably formed in an array 28, where x=(1 to n), and n is the number of resonant members $28(x)$, and preferably further includes a movable, e.g., pivotable clamp member 24. Preferably, the plurality of resonant members $28(x)$ a laminate made by a known process. For example, each resonant member $28(x)$ can be laminated by a lamination process to an adjacent resonant member $28(x)$. The laminate or lamination is preferably a flexible bonding allowing for motion of one resonant member $28(x)$ relative to an adjacent resonant member $28(x)$. The laminate preferably has multiple layers.

As illustrated, control module 14 may include a power cord 15 for engagement with an electrical outlet (not shown). Alternately, control module 14 may be adapted to receive power from a battery pack or from an a/c generator. It is also envisioned that a generator or other power source may be incorporated into control module 14.

Control module 14 includes an electronic signal generator (not shown) and preferably electronic control circuitry to drive a transducer (not shown) positioned on instrument 12 at one or more ultrasonic frequencies. Protective circuitry is preferably provided to prevent injury to a patient, a surgeon or system hardware. Control module 14 also includes display circuitry and hardware (not shown) to provide information to and accept information from a user. This information may be obtained from sensors (not shown) positioned on the instrument end effector. The sensors may be provided to monitor the temperature, density, or ultrasonic or electric impedance, of the tissue being operated on.

Feedback circuitry may be provided to interact with any sensors provided to provide more effective ligation, cutting, dissection, coagulation, etc. For example, the feedback circuitry may terminate operation of the system if a sensor indicates that tissue temperature, density, or ultrasonic or electrical impedance has exceeded a predetermined maximum. The ultrasonic impedance increases as tissue hardens due to rising temperatures. Similarly, electrical impedance is reduced when tissue water level is decreased due to overheating. The feedback circuitry may be selectively activated and deactivated and/or controlled or monitored by a surgeon to provide a surgeon more flexibility in operating the instrument. Further, control module 14 may include diagnostic circuitry to aid in testing and/or debugging instrument 12 or its hardware.

It is contemplated that operation of ultrasonic instrument 12 may be automatically controlled through the use of a computer. In one preferred alternative embodiment of the presently disclosed system, a computer 21 receives data from sensors positioned on the end effector of the ultrasonic instrument. As discussed above, sensors may be provided to monitor different characteristics of the tissue being operated upon including, inter alia, temperature and/or ultrasonic or electrical impedance. Computer 21 preferably includes circuitry to process an analogue signal received from the sensor(s) and to convert the analogue signal to a digital signal. This circuitry may include means to amplify and filter the analogue signal. Thereafter, the digital signal can be evaluated and operation of the ultrasonic instrument can be modified to achieve the desired effect in or on the tissue and prevent damage to surrounding tissue. Computer 21 may be incorporated into control module 14 or linked to control module 14 to effect the desired or appropriate modification of the operation of the instrument 12.

Figure 2:
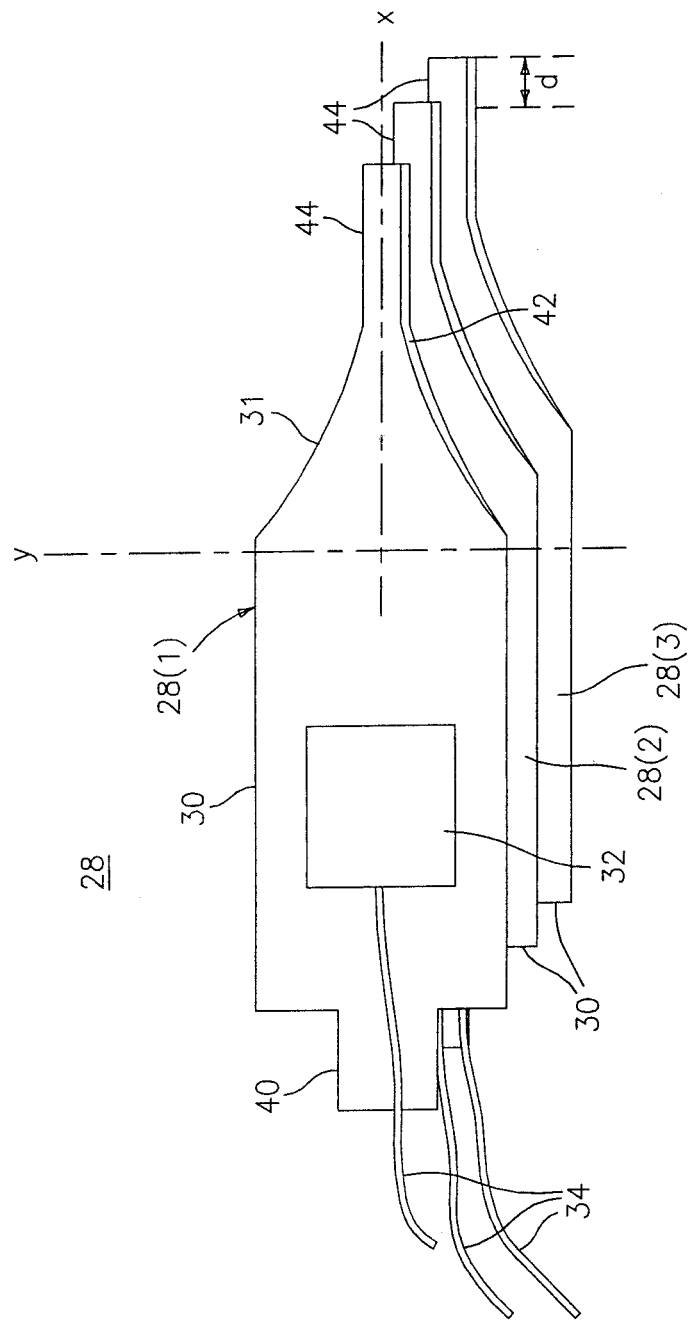
FIG. 2 is a schematic top or side representation of one preferred embodiment of a plurality of resonant members of the presently disclosed ultrasonic surgical instrument.

FIG. 2 shows three exemplary resonant members 28(1-3). Instrument 12 may be configured with an array 28 having a different number of resonant members 28(x). The resonant members 28(1-3) can be positioned side by side so that they are transversely close to one another. The resonant members 28(x) are bonded or attached to one another and mounted as one unit within elongated body 20 of the ultrasonic instrument 12, or alternatively, the resonant members 28(x) are detached from one another and mounted individually within the body 20 of the ultrasonic instrument 12.

Proximal ends of the resonant members 28(x) are staggered relative to adjacent resonant members 28(x), and preferably the staggering distance d is uniform for each pair of adjacent resonant members 28(x), where the distance d is determined by the number of resonant members 28(x) in the array 28, and the wavelength of displacement curves of the resonant members 28(x), as described below with respect to FIG. 4. Transducers 32 (one is shown) can be identically located on each respective ultrasonic member element 28(x). Alternatively, the positioning of the transducer 32 on each resonant member 28(x) may be staggered by a distance d. The lengths of the resonant members 28(x) may be uniform or may be variable. Thus, the distal ends of the resonant members 28(x) may be even with one another, or may be staggered. It is contemplated that the resonant members 28(x), respectively, may have a variety of shapes.

The resonant members 28(x) preferably form a laminate. The laminate is formed by any known process, such as a lamination, some type of bonding, extrusion, injection, molding or combination thereof. Preferably the resonant members 28(x) are bonded to one another by a flexible material that allows movement of one resonant member 28(x) relative to another resonant member 28(x), the relative movement typically being on the order of microns. The positioning of the bonding material for bonding adjacent resonant members 28(x) may vary with respect to design considerations, and thus the percentage of facing surface areas of adjacent resonant members 28(x) having bonding material applied thereto may vary.

Resonant members 28(1-3) of instrument 12 are preferably configured using Micro Electrical Mechanical Systems (MEMS) technology. Resonant members 28(1-3) each include a body portion 30 and a resonant structure 31. In the MEMs configuration shown, a transducer 32, is supported on, located between, or bonded to or within the body portion 30 of each resonant member 28(1-3). The transducer 32 associated with each respective resonant member 28(x) can be an array of transducers.

Transducer 32 can be positioned on, within or adjacent resonant member 28(1) to effect vibration along any axis, e.g., the x-axis, the y-axis, the z-axis or any axis in between the x, y and z axes. Resonant member 28(1) includes an operating surface generally designated 42 configured to effect dissection, cutting, coagulation, ligation and/or to effect hemostasis of tissue. Alternately, resonant member 28(1) may include multiple operating surfaces to perform different tasks, e.g., cutting and coagulation. System 10, including instrument 12, can be used in a variety of surgical applications including general procedures, gynecologic, urologic, thoracic, cardiac and neurological surgical procedures. Instrument 12 may be configured to perform both endoscopic and open surgical procedures and may be actuated via a finger switch or a foot pedal in a known manner. The actuation device may include wireless transmission circuitry to effect actuation of instrument 12.

Each transducer 32 receives an electrical signal from the electronic signal generator (not shown) in control module 14, causing each transducer 32 (such as via piezoelectric or magnetostrictive elements) to be electrically excited. Each transducer 32 converts the electrical signal into mechanical energy resulting in vibratory motion of an ultrasonic frequency of transducer 32 and resonant member 28(1). Ultrasonic member 28(1) may be vibrate in both high and low frequency ranges. In the low frequency range, approximately 20-100 KHz, the instrument will cause cavitation in tissue to effect cutting of the tissue. In the high frequency range, greater than 1 MHz, the instrument may be used for heating and coagulation of tissue. The high and low frequency actuation may occur simultaneously by an electronic power amplifier, capable of generating both frequencies. The vibratory motion is preferably primarily in a longitudinal direction. It is contemplated that the vibratory motion is a transverse motion, such as in Balamuth vibrations.

Figure 3:
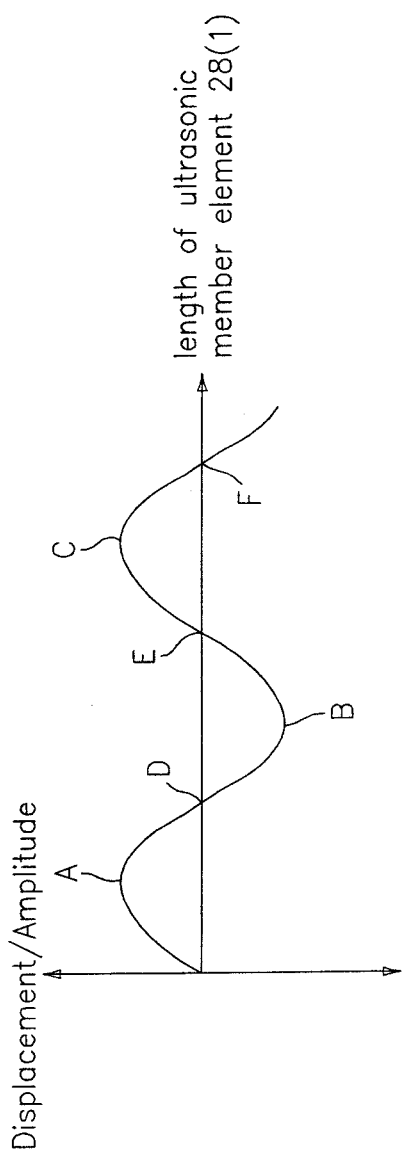
FIG. 3 is a plot of a displacement curve of a vibrating resonant member of the ultrasonic member of the presently disclosed ultrasonic surgical instrument.

FIG. 3 shows a plot of a displacement curve along a vibrating resonant member 28(1). The y-axis is the displacement/amplitude of the vibrations, and the x-axis is the length of the resonant member 28(1). The plot is sinusoidal by nature with respect to amplitude of the vibrations, and the amount of motion of the resonant member 28(1) varies along the length of the resonant member 28(1). The amplitude of the curve corresponds to the amount of displacement of the vibrating resonant member 28(1). Points A, B and C of the resonant member 28(1) are points of maximum motion (also known as anti-nodes), and points D, E and F of the resonant member 28(1) are points of substantially no motion where the amplitude of the curve is zero (also known as nodes).

Preferably transducers 32 are piezoelectric transducers. Alternately, other transduction mechanisms, other than piezoelectric, may be used including thermal stress, electrostriction, magnetostriction or optical drive mechanisms. Transducers 32 are connected to the electronic signal generator and control module 14 by an electrical connector, preferably cables 34. Cables 34 may be merged with cable 16. Cables 34 may extend proximally from transducers 32 through the body 20 of instrument 12 (FIG. 1) and exit instrument 12 through an opening (not shown) in the handle assembly 18 of the instrument for connecting to the electronic signal generator. As shown in FIG. 3, one cable is provided for each transducer 32, with a first end connected to the electronic signal generator, and a second end connected to a respective transducer 32. In another embodiment one cable 34 is provided, which is connected to the electronic signal generator at a first end and at a second end branches into a plurality of cable branches 34a, with each cable branch 34a connected to one transducer 32 of the array of transducers.

Figure 4:
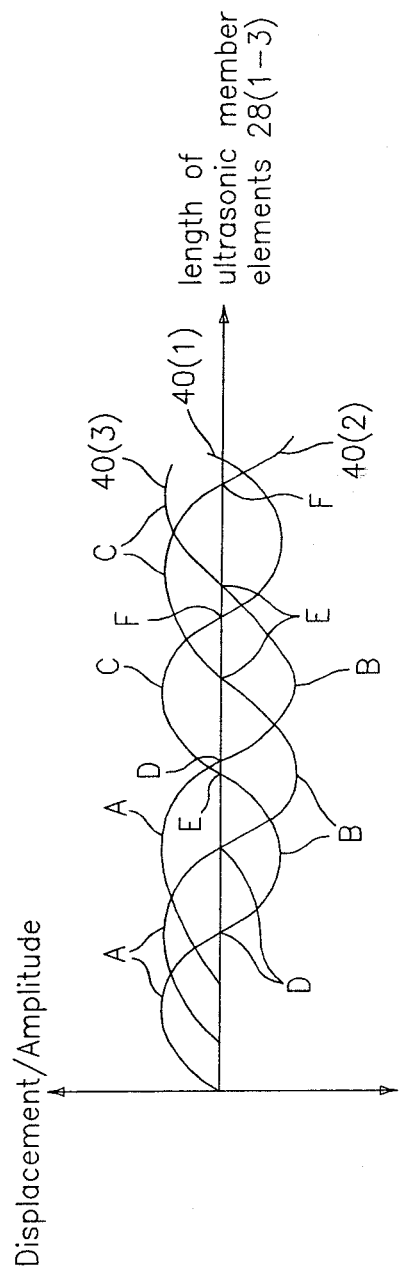
FIG. 4 is a plot of a displacement curve of multiple vibrating resonant members of the ultrasonic member of the presently disclosed ultrasonic surgical instrument.

FIG. 4 shows a plot of displacement curves 40(1-3) along vibrating resonant members 28(1-3), respectively, where the relative offset of the curves 40(1-3) is caused by staggering of the resonant members 28(1-3) with respect to each other along the longitudinal axis. The curves 40(1-3) are offset from one another such that maximum points A, B, C of each curve are offset from maximum points A, B, C of the other curves, respectively, and likewise for the minimum points D, E, F.

Along the length of the array 28, the combined (i.e. summed) displacement curves 40(1-3) do not have any nodes where the combined amplitude=0, and therefore the net displacement of the vibrating array 28 is always nonzero. Thus, the along the entire length of the array 28 there is net vibrational motion, which increases the effective length of the array 28 relative to a conventional ultrasonic member having only one vibrating element. The length of the array 28 may be extended indefinitely such that there is net vibrational motion along the entire length of the array 28 without any regions of zero motion.

Furthermore, along the length of the array 28, the combined displacement curves 40(1-3) have much less variation in amplitude than a single combined displacement curve, and therefore the net motion along the vibrating array is relatively consistent with respect to an ultrasonic member having only one vibrating element.

The offset between displacement curves having wavelength $\lambda$ of n resonant members is preferably $\lambda/n$. Thus, the distance d in FIG. 2 is $\lambda/3$. Likewise, for an array having n resonant members 28(x), the distance offset d is preferably $\lambda/n$. In another embodiment, the distance d may be selected to be other than $\lambda/n$, and the offset of the displacement curves of the n vibrating resonant members 28(x) may be different from $\lambda/n$.

In another embodiment, the displacement curves for different resonant members 28(x) have different wavelengths and/or different amplitudes. An ultrasonic member 28(x) caused to vibrate at more than one frequency may have more than one displacement curve, the displacement curves having different wavelengths. For example, the different transducers 32 of the array of transducers may generate vibrations having different frequencies, such as by altering the input to the transducer, or having differently configured transducers. Alternatively, circuitry may be provided for altering the frequency, waveshape or amplitude, superimposing more than one frequency or a combination thereof of the vibrations generated by the transducers 32. Accordingly, the vibration of the resonant members 28(x) may be other than sinusoidal.

It is contemplated that other means may be provided for offsetting the displacement curves of resonant members 28(x) relative to one another, instead of staggering the resonant members 28(x) longitudinally. For example, delay circuitry may be provided to at least one of the lines providing input or output to the transducers 32 or within the transducer. In another embodiment a control unit is provided for controlling operation of the transducer and/or delay circuitry for effecting offsets of the displacement curves.

In conventional instruments the transducer is traditionally attached to the proximal end of the hand piece and connected to the end effector of the instrument via an elongated vibration coupler. It is contemplated that the array of transducers of the present invention may be positioned similarly to the transducer of the conventional instruments, and that a vibration coupler be provided to connect each transducer of the array to a respective resonant member 28(x) mounted at the distal end of the instrument 12.

For MEMs configurations in which the transducers 32 are positioned on, between, or in the resonant members 28(x) adjacent the distal tip of the instrument, the following benefits can be realized: a) the need for an elongated vibration coupler formed of titanium is obviated substantially reducing the cost of the instrument; b) the length of the body portion of the instrument can be changed, e.g., shortened or lengthened, with virtually no consequential change in instrument performance, e.g., since the instrument vibration coupler has been replaced by an electrical conductor, the instrument need not be retuned, at considerable expense, after changes in body length; c) ultrasonic energy can be transferred to a patient more efficiently, thus lowering energy power requirements; d) the portion of the instrument that is disposable can be easily varied and may comprise only the instrument tip with a limited reuse handle, the entire instrument or any degree of disposability therebetween; e) because the handle assembly does not support the transducer, the handle assembly can be eliminated or more ergonomically configured; and f) the use of a small transducer on, in or adjacent the distal end of the instrument in place of a large transducer on the proximal end of the instrument substantially reduces the weight of the instrument and makes it easy to manage especially during delicate surgical procedures.

The resonant structure 31 of each of the resonant members 28(x) is preferably formed of a silicon or metal resonant structure or a silicon/metal composite. Alternately, materials such as titanium or other metals may be bonded or joined in some manner to the silicon to improve fracture resistance. It is envisioned that materials other than silicon which are suitable for ultrasonic use may be used to form resonant structure 31.

The resonant structure 31 may be formed using an etching process, e.g., isotropic etching, deep reactive ion etching, etc. Suitable etching processes are disclosed in U.S. Pat. No. 5,728,089 filed Oct. 31, 1994, which is also incorporated herein in its entirety by reference. Alternately, other known means may be used to form the ultrasonic member including a variety of different mechanical processes.

Figure 5A:
FIG. 5A is a side view of one preferred alternate embodiment of the resonant member of the presently disclosed ultrasonic surgical instrument.
Figure 5B:
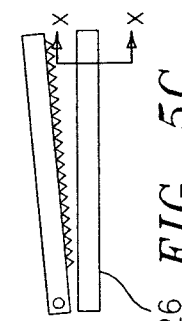
FIG. 5B is a side view of another preferred alternate embodiment of the resonant member of the presently disclosed ultrasonic surgical instrument.
Figure 5C:
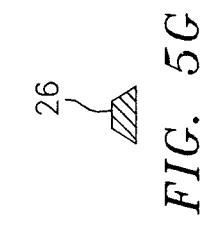
FIG. 5C is a side view of another preferred alternate embodiment of the resonant member of the presently disclosed ultrasonic surgical instrument.
Figure 5D:
FIG. 5D is a cross-sectional view taken along section lines X-X in FIG. 5C.
Figure 5E:
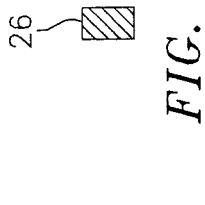
FIG. 5E is a cross-sectional view of an alternate embodiment of the ultrasonic member shown in FIG. D as would be seen along section line X-X of FIG. 5C.
Figure 5F:
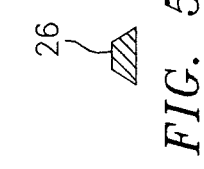
FIG. 5F is a cross-sectional view of an alternate embodiment of the ultrasonic member shown in FIG. D as would be seen along section line X-X of FIG. 5C.
Figure 5G:
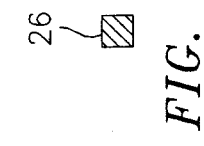
FIG. 5G is a cross-sectional view of an alternate embodiment of the ultrasonic member shown in FIG. D as would be seen along section line X-X of FIG. 5C.
Figure 5H:
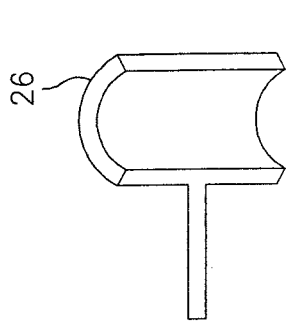
FIG. 5H is a top view of another alternate embodiment of the presently disclosed ultrasonic member.
Figure 5I:
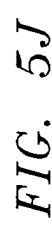
FIG. 5I is a side perspective view of another embodiment of the presently disclosed ultrasonic member.
Figure 5J:
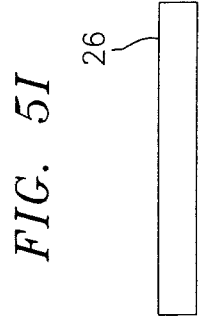
FIG. 5J is a side perspective view of another embodiment of the presently disclosed ultrasonic member.
Figure 5K:
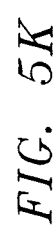
FIG. 5K is a side view of another embodiment of the presently disclosed ultrasonic member.

The resonant structure 31 is shown as a linear blade having an operative surface 44 (FIG. 2). FIGS. 5A-K show alternate configurations of the resonant structure 31 of resonant members 28(x), including, inter alia, J-hook (FIG. 5A), L-hook (FIG. 5B), shears (FIG. 5C) having a variety of different cross-sectional shapes (FIGS. 5D-5G), spatula (FIG. 5H), arcuate (FIGS. 5I and 5J) and rectangular (FIG. 5K). The end effector may also be configured to have a curved blade such as the blade disclosed in U.S. Pat. No. 6,024,750, filed on Aug. 14, 1997 and/or an angled blade, such as disclosed in U.S. Pat. No. 6,036,667, filed on Oct. 4, 1996, both of which are incorporated herein in their entirety by reference.

Each of resonant members 28(x), or array 28 as an integral unit, may be attached to a distal portion of instrument 12 in any known manner. For example, each of resonant members 28(x) or the integral array 28 may be secured to a substrate or shaft or a mounting member (not shown) supported within a distal end of body 20 of instrument 12 such as by a snap-fit connection, a set screw or crimping or swaging. A threaded shank 40 or other attachment structure formed on or disposed on or in a proximal end of each of resonant members 28(*x*) or integral array 28 may be provided for attachment of the resonant members 28(*x*) or array 28 to the distal end of instrument 12.

Figure 6:
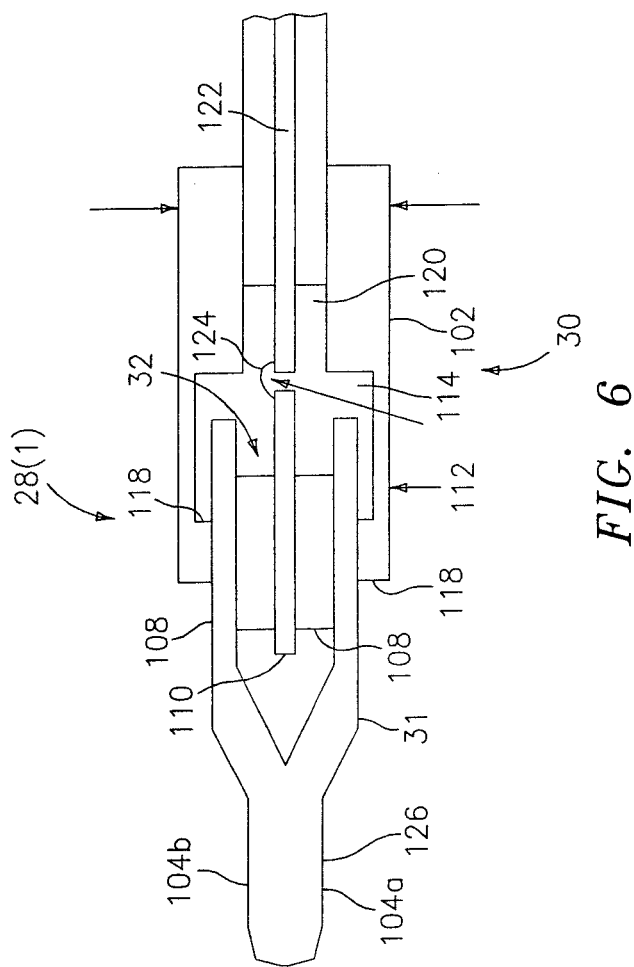
FIG. 6 is a top or side schematic representation of a preferred embodiment of the ultrasonic member of the presently disclosed ultrasonic surgical instrument.

FIG. 6 illustrates one preferred embodiment of resonant member 28(1) configured in the MEMs configuration and suitable for use in the presently disclosed ultrasonic surgical instrument of ultrasonic surgical system 10. Preferably resonant members 28(2-*n*) (not shown) have similar embodiments. Resonant member 28(1) is preferably a piezoelectric laminate structure which includes a body 30 having frame 102, a resonant structure 31, and a transducer 32. Transducer 32 preferably includes a pair of PZT crystals 108 separated by silicon plate 110. Alternately, it is envisioned that crystals other than PZT crystals may be used to convert electrical power to effect mechanical vibration. An appropriate bonding agent or process, e.g., solder bonding, diffusion bonding, adhesives, etc., is used to fasten crystals 108 to plate 110.

Resonant structure 31 preferably includes at its distal end first and second resonant members 104*a* and 104*b*. The proximal end of resonant members 104*a* and 104*b* together define a cavity for receiving transducer 32. Alternately, resonant structure 31 may be monolithically formed from a single piece of material. The mating surfaces of PZT crystals 108 and resonant members 104*a* and 104*b* are fastened together using an appropriate flexible bonding agent or bonding process, e.g., glass binding, adhesives, etc.

Frame 102 includes a body 112 which is preferably formed from a rigid material including metals, ceramics, etc. and includes a cavity 114 dimensioned and configured to receive the resonant structure 31 and transducer 32 assembly. A bonding layer or layers 118, preferably formed of a conductive material, is positioned between the proximal portion of resonant members 104*a* and 104*b* and frame 102 to bond transducer 32, which is movable, to frame 102, which is stationary. The proximal end of frame 102 includes a throughbore 120 which is dimensioned to permit passage of an electrical conductor 122, e.g., a wire or coaxial cable, to provide power to transducer 32. The electrical conductor is preferably a high-voltage high-frequency Teflon insulator cable, although the use of other conductors is envisioned. The distal end of conductor 122 is connected to plate 110 by a flexible conductive wire 124 which does not restrict relative movement between frame 102 and transducer 32.

As discussed above, the shape of resonant structure 31 may be different than that shown in FIG. 6. More specifically, distal operating surface 126 of resonant structure 31 may assume any of the configurations shown in FIGS. 5A-5K or any other configuration not shown herein which may be advantageous for performing a particular surgical procedure. Moreover, a clamp may be provided to facilitate gripping of tissue.

In the preferred embodiment, proximal ends of resonant members 104*a* and 104*b* of a first resonant member 28(1) of an array 28 of resonant members 28(*x*) are staggered relative to the proximal ends of a second resonant member for effecting an offset in displacement curves of the respective resonant members.

It will be understood that various modifications may be made to the embodiments disclosed herein. For example, the configuration of the ultrasonic member of the end effector need not be as shown herein but rather may be any that is suitable for the particular surgical application. Further, the transducer may be mounted proximally of the ultrasonic member of the end effector in the distal end of the instrument and need not be mounted directly to the ultrasonic member. Therefore, the above description should not be construed as limiting, but merely as exemplifications of preferred embodiments. Those skilled in the art will envision other modifications within the scope and spirit of the claims appended hereto.

What is claimed is:

1. An end effector of an ultrasonic surgical instrument, the end effector comprising:
    an array of at least two resonant members, each resonant member including
        a body defining a first cavity at a distal end of the body;
        a resonant structure defining a distal end and a proximal end, the proximal end of the resonant structure received within the first cavity, the distal end of the resonant structure extending longitudinally and distally beyond the first cavity, the resonant structure defining a second cavity at the proximal end of the resonant structure; and
        a transducer received within the second cavity, the transducer effecting vibrations along the length of the resonant member;
    wherein the at least two resonant members are staggered longitudinally relative to each other, and wherein a displacement curve associated with the vibrations of one of the at least two resonant members is offset relative to a displacement curve associated with the vibrations of another of the at least two resonant members.

2. The end effector of claim 1, wherein the combined displacement curves of each of the at least two resonant members is always nonzero.

3. The end effector of claim 1, wherein the vibrations are longitudinal.

4. The end effector of claim 1, wherein the vibrations are transverse.

5. The end effector of claim 1, wherein one of the at least two resonant members is bonded to another of the at least two resonant members by a flexible bond.

6. An end effector of an ultrasonic surgical instrument, the end effector comprising:
    a first resonant member operatively connected to a first transducer and a second resonant member operatively connected to a second transducer, each transducer effecting vibrations along the length of the corresponding resonant member;
    wherein each resonant member includes a body portion and a resonant structure, the resonant structure extending longitudinally and distally from the corresponding body portion, the resonant structure having at least two operative surfaces each configured to perform a different task, and each transducer being directly attached to a body portion of the corresponding resonant member;
    wherein the first transducer is staggered longitudinally with respect to the second transducer resulting in a relative distance between the transducers along a longitudinal axis of the end effector, the relative distance remaining substantially the same during vibrations of the resonant members.

7. The end effector of claim 6, wherein the vibrations are longitudinal.

8. The end effector of claim 6, wherein the vibrations are transverse.

9. The end effector of claim 6, wherein the first resonant member is bonded to the second resonant member by a flexible bond.

* * * * *